United States Patent [19]

Merlette

[11] Patent Number: 4,959,073
[45] Date of Patent: Sep. 25, 1990

[54] FOOT PROSTHESIS AND METHOD OF MAKING SAME

[76] Inventor: John Merlette, 1208 E. Mockingbird Ln., Sandy, Utah 84070

[21] Appl. No.: 202,821

[22] Filed: Jun. 6, 1988

[51] Int. Cl.$^5$ .............................................. A61F 2/66
[52] U.S. Cl. ........................................ 623/55; 623/27
[58] Field of Search .................................. 623/27–32, 623/53–55

[56] References Cited

U.S. PATENT DOCUMENTS

| | | |
|---|---|---|
| 366,494 | 7/1887 | Marks . |
| 1,013,828 | 1/1912 | Thomas . |
| 2,440,075 | 4/1948 | Campbell . |
| 3,889,301 | 6/1975 | Bonner, Sr. . |
| 4,397,048 | 8/1983 | Brown et al. . |
| 4,547,913 | 10/1985 | Phillips . |
| 4,645,509 | 2/1987 | Poggi ................................. 623/55 |
| 4,822,363 | 4/1989 | Phillips ............................... 63/27 |

FOREIGN PATENT DOCUMENTS 25322 1/1923 France .

Primary Examiner—Richard J. Apley
Assistant Examiner—James Pvizant
Attorney, Agent, or Firm—Robert R. Mallinckrodt; Philip A. Mallinckrodt

[57] ABSTRACT

A foot prosthesis comprising an elongate composite main member having a leg section and a toe section with one end of the leg section adapted to be connected to an amputation socket and the other end smoothly curving forwardly through an ankle section into the toe section and extending to a toe end, and a heel member extending from the toe end rearwardly generally along the toe section and then diverging from the toe section and extending to a heel tip. The main member and heel member are preferably of one piece construction with continuous fibers of the composite material extending through the main member and around the toe tip and through the heel member. A resilient material, such as rubber, is bonded between the toe section and heel member where the two are generally adjacent and the properties of the resilient material may be made adjustable by the wearer where the toe section and heel member diverge. In making the prosthesis, the uncured composite material is layed up with uncured rubber in desired position and the two materials cured together. It is preferred that the prosthesis device be removably attachable to an amputation socket by means of an aligned recess in the amputation socket which securely accepts the upper end of the leg portion of the main member.

15 Claims, 3 Drawing Sheets

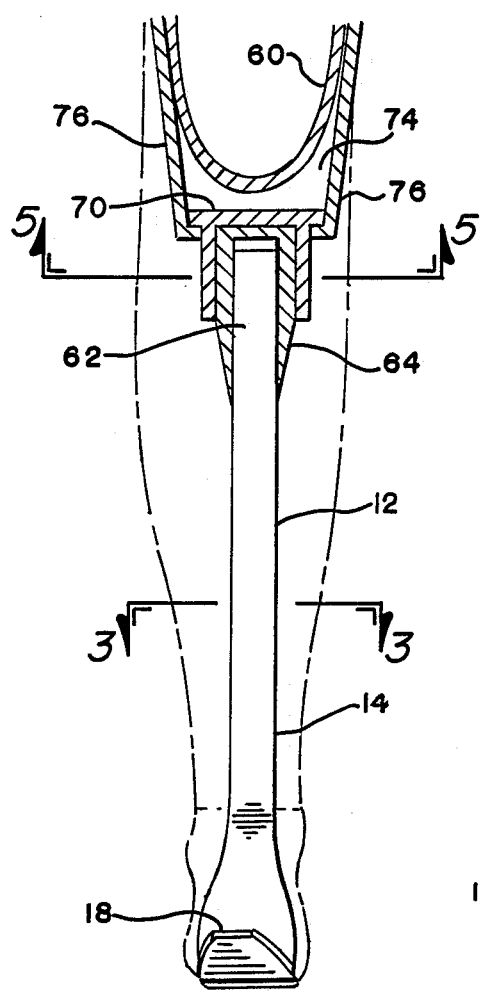
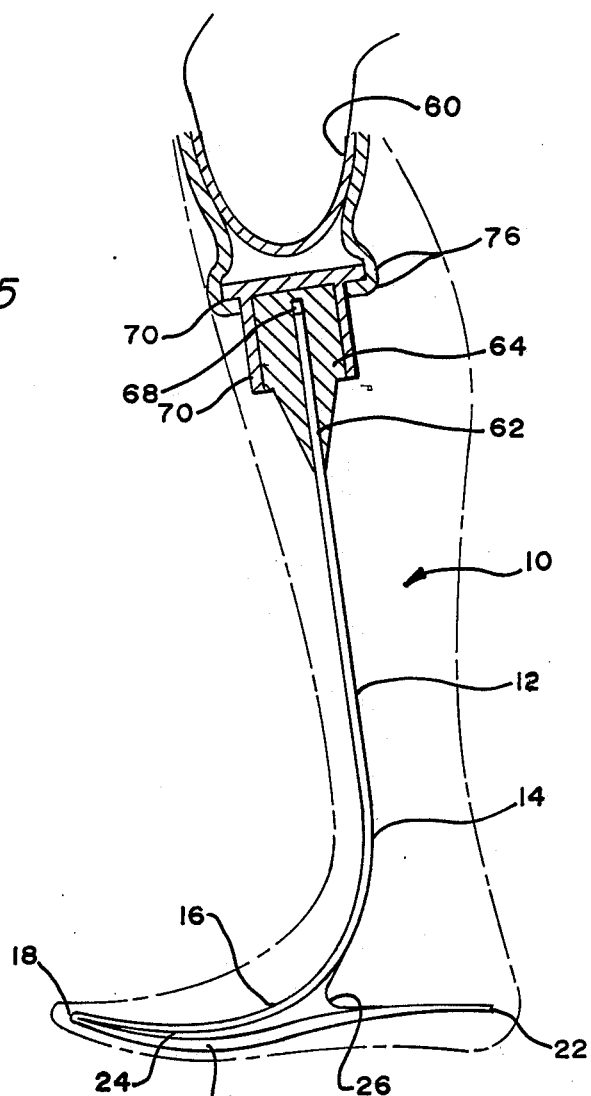
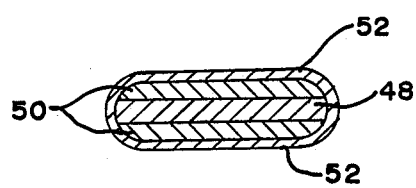
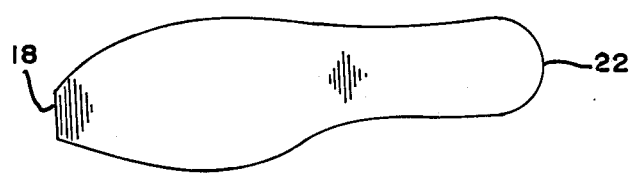
FIG. 2
FIG. 1
FIG. 3
FIG. 4

FOOT PROSTHESIS AND METHOD OF MAKING SAME

BACKGROUND OF THE INVENTION

1. Field:

The invention is in the field of foot prosthesis which attach to an amputation socket and provide an artificial leg and foot to a wearer.

2. State of the Art:

There are a number of different foot and leg prosthetic devices currently in use. The primary goal of these devices is to extend an amputated leg to the ground so as to support the wearer while upright. The earliest prior art was merely a peg secured to the amputation which provides minimal mobility to the wearer. Later, a foot was added to the bottom of the peg. An example of a more modern basic foot prosethsis known as the "Sach Foot" is a carved wooden foot with an aluminum strut attaching the foot to the amputation socket. Additional improvements made to the basic device by way of ankle hinges or ball joints, improve mobility but the overall prosthesis remains rigid and heavy and as such remains uncomfortable to the wearer. Recent studies indicate such rigid systems contribute to premature hip deterioration due to severe axial loads transmitted to the wearer's hip joint.

Recent improvements to foot prosthesis configurations utilize modern composite material technology to impart energy storage and release during use. Examples of these are the so called "Seattle Foot," which is a molded plastics foot and the prosthesis shown in U.S. Pat. No. 4,547,913, known as the Flex-Foot, which provides a composite strut and foot configuration. The spring like action imparted by the materials used results in additional mobility and comfort to the wearer. However, such prior art retains certain design characteristics which limit its potential usefulness and prevent ideal optimization possible with modern high performance composite materials. All known devices within this group are made up of individual components that must be fastened together, be it the heel-to-foot or the foot-to-connecting leg extension. These joints must be rigidly constructed so as to be strong enough to withstand the concentrated loads transmitted through them. The result is that local stiffness occurs which interferes with smooth, even flexing of the components during the wearer's stride. Even with the rigidly constructed joints, these devices are prone to fatigue and fracture at the joints thus placing the wearer at risk of injury.

In addition, composite materials exhibit poor bearing strength where fasteners penetrate the construction. The accumulative wear and erosion of structural material surrounding fasteners result in loss of position or support of attached components after a period of continual use. The fastening of the heel to the ankle portion of the foot as in U.S. Pat. No. 4,547,913 occurs at the highly stressed ankle zone. To prevent fracture, the buildup of materials required for strength makes attractive cosmetic finishing of the ankle area difficult.

With currently known prosthesis, the prosthesis is fitted directly to the amputation socket and once the prosthesis is attached to the socket, it cannot be removed. Any change of prosthesis requires a complete change of the amputation socket along with the prosthesis. The fitting of the prosthesis to the amputation socket requires careful alignment and adjustment and is thus expensive. With current prosthesis, each prosthesis must be separately fitted and secured to its own amputation socket. Because of this, many prosthesis wearers cannot afford a variety of prosthesis such as one for sporting activities, one for normal walking, and one for dress wear. Since different characteristics are desirable for prosthesis for different uses, it would be desirable for a wearer to be able to easily adjust the characteristics of a prosthesis for an intended use or to be able easily change prosthesis for the intended use. Presently, if a user engages occasionally in vigorous sports activities, his prosthesis has to be strong enough to withstand such activity. However, a prosthesis designed for active sports is generally stiffer than that required for normal walking, is uncomfortable for normal walking, and generally unsuitable for use with fashion footwear. However, a softer, more complaint prosthesis for normal wear generally cannot take the forces applied during vigorous sports activity. There is currently no prosthesis which provides a means for the wearer to adjust the characteristics of the prosthesis, and it is difficult to change the prosthesis each time an activity changes.

SUMMARY OF THE INVENTION

According to the invention, a foot prosthesis provides a more natural feel and maintains more uniform and controllable flexibility than prior art prosthesis through a unitary composite construction from attachment to the amputation socket through the ankle area and extending to the toe section of the prosthesis. The heel member preferably is a unitary continuous extension of the prosthesis from the tip of the toe rearwardly back along a portion of the toe section and then to the heel tip with a resilient material secured between the heel member and adjacent portion of the toe member. An attachment means is secured to the amputation socket so that different prosthesis may be easily attached or removed as desired by the wearer.

In a preferred embodiment of the invention, the prosthesis is molded by positioning continuous fibers, embedded in an epoxy resin matrix, along the vertical length of the leg section of the prosthesis, through the ankle area, across the top of the foot to the toe, and then sharply back to the heel tip to form a one piece composite structure without separate sections fastened together. Where the heel member extends back from the tip of the toe section, the heel and toe sections are sustantially adjacent and a resilient material such as a rubber pad is integrally molded into the structure between the heel member and the toe section along this area of adjacency. The rubber pad imparts flexibility and an integrity to the device along it s heel-to-foot junction to better handle and absorb heel side or torque loads which may be applied at the heel or axially along the leg section. The rubber pad also provides energy dampening and increased comfort to the wearer. In one embodiment, the rubber pad is made adjustable near its end where the toe and heel sections begin to diverge by means of providing an opening in the rubber pad and removable plugs of varying resilient properties which fit into the opening to thereby vary the properties of the rubber pad in that area and to effectively shift the fulcrum point of the heel. This results in a change of effective heel length and results in an adjustment of heel stiffness to optimize the performance and comfort of the prosthesis for varying activities.

The construction described provides a prosthesis with more dynamic performance that closely simulates the complex muscular-skeletal heel and ankle performance.

The attachment means secured to the amputation socket is specially fitted for the user and provides an aligned recess for receiving the top of the prosthesis. When the prosthesis is inserted into the receiving recess, it is securely held in the preset alignment with the amputation socket. In this way, a single fitting can be made to fit and align the receiving recess properly with the amputation socket and several prosthesis provided to fit into the recess. Thus, the expensive fitting process is done once and additional fitting for each separate prosthesis are avoided.

In making the prosthesis, the main member and heel member are both layed up of uncured composite material and uncured rubber is inserted into the area desired between the generally adjacent portions of the toe section and heel member. The composite material and uncured rubber are then cured together.

THE DRAWING

In the accompanying drawings, which illustrate the best mode presently contemplated for carrying out the invention:

FIG. 1. is a side elevation of the fully assembles foot prosthesis showing the attachment means and amputation socket in section;

FIG. 2, a front elevation of the embodiment of FIG. 1, again showing the attachment means and amputation socket in section;

FIG. 3, a transverse section taken on the line 3—3 of FIG. 1;

FIG. 4, a bottom plan view of the device of FIG. 1;

FIG. 5, a transverse section taken on the line 5—5 of FIG. 1;

FIG. 6, a fragmentary side elevation of an alternate embodiment which includes a removable plug in the area between the heel and toe section of the device;

FIG. 7, a fragmentary vertical section taken on the line 7—7 of FIG. 6 and showing a rubber plug in position in a receiving opening of the device;

FIG. 8, a fragmentary perspective view of the device of FIG. 1 showing a cosmetic cover molded directly onto the foot; and FIG. 9, a perspective view of an alternate embodiment of the prosthesis of the invention.

DETAILED DESCRIPTION OF THE ILLUSTRATED EMBODIMENT

Figure 5:
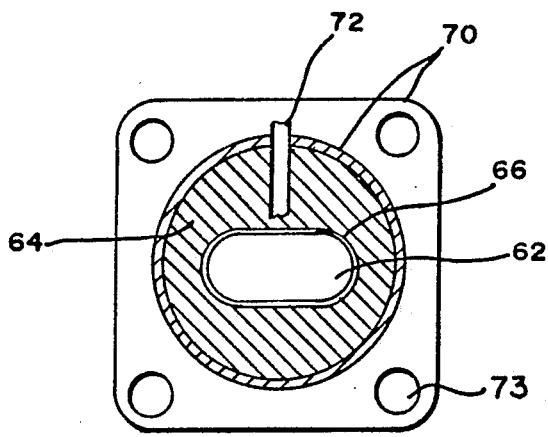

As shown in FIGS. 1 and 2, a prosthesis of the invention includes a composite main member 10 having a leg section 12, an ankle section 14 and a toe section 16 extending to a toe tip 18. A heel member 20 extends from toe tip 18 backwardly to heel tip 22 with the forward portion of heel member 20 extending along and generally adjacent to toe section 16 until toe section 16 turns upwardly toward ankle section 14 at which point toe section 16 and heel member 20 diverge. Main member 10 is of single piece composite construction and preferably member 20 is constructed as a continuation of main member 10 so that the leg section 12, ankle section 14, toe section 16 and heel member 20 are formed as a single piece. This eliminates any mechanical fastening or binding together of separate components and provides a uniform flexure sequence for the device. Main member 10 and heel member 20 are constructed of either carbon, fiberglass, or aramid continuous fibers in an epoxy resin which surrounds and escapsulates the individual fibers. One or more of the fiber types may be utilized alone or together in the construction of the device, each imparting its own unique properties of strength, stiffness, toughness, and density to achieve the desired overall performance characteristics of the device. The continuous filaments extend uninterrupted from the top of leg portion 12 downwardly through the ankle section 14, across the top of the foot or toe portion 16 to the toe tip 18 and then rearward through the heel member to heel tip 22.

A resilient material 24, such as a flexible rubber, is adhered between the adjacent portions of the toe section 16 and heel member 20. As shown, this material extends from the inside of toe tip 18 back to the area where the toe section and heel members diverge. The resilient material 24 substantially maintains the relative positions of the upper and lower portions of the more rigid composite parts. Being much softer than the composite material, it allow deflection of the composite material without substantial interference and yet, under torsional load, has the strength to prevent the composite components from separating. Under load, the composite components tend to flex in opposite directions relative to each other. The resilient interface will elongate but retain the bond between the parts. Additionally, the resilient material forms a fulcrum point from which the cantilevered heel will deflect. This fulcrum point will be in the area indicated by 26 where the resilient material ends and from which the heel member extends backwardly to heel tip 22, but varies with the characteristics of the resilient material in that area. With the resilient material, the heel member may be secured at toe tip 18 so as to remain quite flexible. Without the resilient material, the same securement would provide a heel member too flexible to perform satisfactorily. Without the resilient material, the joint between the toe tip and heel and the heel member itself would have to be much more rigid. The resilient material also provides some degree of cushioning to the device upon heel impact.

In the basic construction of the prosthesis, the composite material is finish trimmed so as to closely duplicate the natural foot bottom pattern as shown in FIG. 4. The forward foot portion may be shaped by grinding to satisfy left or right foot configuration requirements, however, the toe portion 18 remains untouched so as to protect the continuous fibers which pass through this area. The heel stiffness, or support capability, is a function of the heel member's width, thickness, and distance of the heel tip 22 from the point of departure 26 from the resilient material. Optimally, the heel stiffness should be sufficient to allow the wearer to walk without his or her shoulder on the side the prosthesis is worn dropping significantly. Shoulder drop is an indication of insufficient heel support. For athletic use, where more severe heel impact occurs, a stiffer heel is desired than for casual use.

With the present invention, since the heel stiffness is dependent to some degree upon the properties of the resilient material where the toe section and heel members diverge, i.e., area 26, in addition to the construction of the heel member itself, i.e., the thickness, width, and material used for the heel member, the heel stiffness can be made adjustable to some degree by making the properties of the resilient material at area 26 adjustable.

Figure 7:
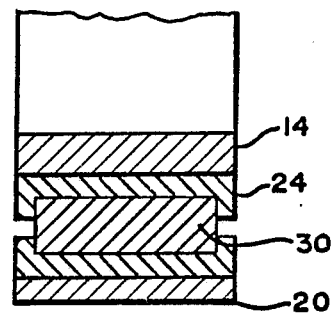
Figure 6:
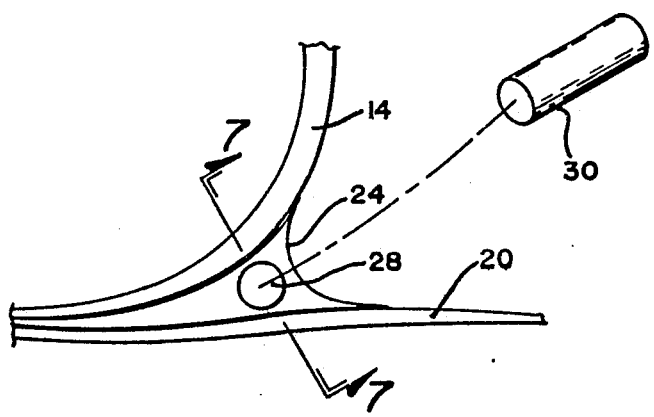

For this purpose, as shown in FIGS. 6 and 7, a cavity 28 may be molded into the rear portion of the resilient material which is adapted to receive a removable plug 30. As shown in FIG. 7, the receiving cavity 28 may be molded with shoulders 32 at each end which, since they are formed of the resilient material, may be stretched to allow plug 30 to be placed in or removed from cavity 28. When plug 28 is in place, the shoulders 32 will hold it in place so it does not fall out during normal use of the prosthesis. By having several plugs 30 of varying properties, such as varying hardness, the heel stiffness of the prosthesis may be varyed by merely changing the plug. Thus, the properties of the prosthesis may be changed for different activities without having to remove the prosthesis and change to an entirely different prosthesis with the desired different properties.

The embodiment in FIG. 6 shows a round plug, and this is presently preferred because it is the most easily fabricated configuration. However, various other configuration could be used duch as a wedge or an oval shape. Variations in plug shape effect the amount of heel stiffness change that will occur when plugs of different properties are inserted.

While various composite construction techniques may be used in forming the prosthesis of the invention, a presently preferred construction is shown in FIG. 3. The central core 48 consists of fiberglass or carbon filaments embedded in an epoxy resin which during construction is in a highly viscous or tacky condition. The state of the art procedure for forming the composite structure is to lay up layers of preformed sheets of the fiber and resin which are cut from supply rolls. This "prepreg", or resin preimpregnated fiber, is commercially available from various suppliers. The ratio of resin to fiber, i.e., resin content, is carefully controlled by the supplier to specifications provided by the prosthesis manufacturer. Tight controls during the preparation of this "prepreg" material assure reproducible prosthesis results. The central core of the prosthesis device of FIG. 3 may also contain a small amount of continuous aramid fibers which, due to their tough nature, will retain the components in their relative structural position should the device be damaged. The central core 48 is sandwiched front and back by layers of carbon fiber composite 50, similar in form to the fiberglass materials previously described. Although the orientation of the fibers, i.e., the direction of the fibers relative to the long axis of the device, may be varied in infinite combinations to satisfy specific performance requirements, for the layers described so far, a generally lengthwise orientation has been found from analysis and testing to work best.

The application of an additional outside layer 52 of diagonally oriented fibers, such as fibers set at forty-five degrees to the length axis of the device, has been found by testing and analysis to be effective in providing torsional stiffness control and stability to the device. It is preferred that these outer fibers completely encircle the inner fibers, as shown, although the outside layer could be provided on just the front and back sides of the member.

The resiliant material, which binds the composite toe section and heel member is formed by laying up thin sheets of uncured "green" natural rubber upon each other in a stack, preferably each ply end offset from the others so as to create a tapered thickness as shown in FIG. 1. With the composite material and rubber in desired position, the device is cured. This is generally done by placing the device, in this state called a laminate, in a forming mold and placing the forming mold into an oven or autoclave and heating it in a vacuum environment to cause a molecular reaction within the resin. The result is a hardening of the resin which stabilizes the fibers thus allowing each fiber to remain positioned as desired, to best transmit applied load in a springlike or elastic state. When cured at the same time as the composite prepreg, the rubber material and the resin material will adhere well to each other and the individual plys of rubber material will reform into one homogeneous elastomeric mass.

The cavity 28 in the rubber material is created during the fabrication process by applying uncured sheet rubber around a metal tooling plug and curing together with the rest of the foot material. After cure, the plug is removed leaving the desired cavity in the rubber.

While the top of the leg portion 12 of the prosthesis may be secured to an amputation socket 60 in any known manner, it is perferred that it be removably secured to the amputation socket so that the prosthesis may be easily removed from the socket and replaced with a similar prosthesis of different properties, when desired by the wearer. The end portion 62 of the upper part of leg section 12 is inserted and bonded to an inner sleeve 64 using an elastomeric adhesive 66. The end portion 62 of the device may be shortened, or spacers 68 may be inserted into the sleeve 64, to adjust foot height prior to bonding. This bonded assembly is then removably inserted in tight fitting relationship in a receiving recess formed by outer housing 70 and is held in such recess by friction and/or a fastener 72 joining sleeve 64 and housing 70. The materials for the housing 70 and sleeve 64 may be molded plastic or metal which exhibit good strength, abrasion resistance and toughness. The special mounting avoids penetration of large fasteners through the structural composite prosthesis.

Installation of housing 70 with prosthesis secured thereto to amputation socket 60 is accomplished using standard alignment devices common to most prosthetist's laboratories. Specifically, the prosthesis assembly, including the housing mounting plate 70, is attached to a standard alignment tool, not shown, through the mounting holes 72, FIG. 5, using screw fasteners. The alignment tool is located between housing 70 and amputation socket 60 in the area indicated as 74, FIG. 1. After the angular and lateral positioning is done in normal manner, the alignment tool is removed and replaced permanently with an overwrap of composite material 76 which, after cure, rigidly positions the attachment housing 70 to the amputation socket 60 as shown in FIGS. 1 and 2.

Some modern lightweight alignment devices presently available commercially are designed to remain permanently is position between housing 70 and socket 60 after positioning takes place. In such instance, composite material 76 may be wrapped over such alignment device to provide reinforcement for the mounting during active sports use.

With any composite prosthesis device, toe impact caused by contact within footwear or "stubbing" the uncovered foot can cause accelerated degradation of the composite materials. Such degradation is resisted in the invention by the preferred toe formation wherein the composite fibers do not terminate at the tip of the toe, but extend as continuous fibers back to the heel. This gives superior resistance to ply separation which is a problem in the prior art where the fully trimmed toe area edge exposes the full ply lamination.

An alternate method employed to achieve protection at the toe is to slip fit a tough, molded plastic cap over the toe end. The plastic cap may be similar to caps commonly used on snow skis. Molded left or right-hand caps could also aid in development of a limited selection of "universal" foot configurations if such an approach were taken for production.

Figure 8:
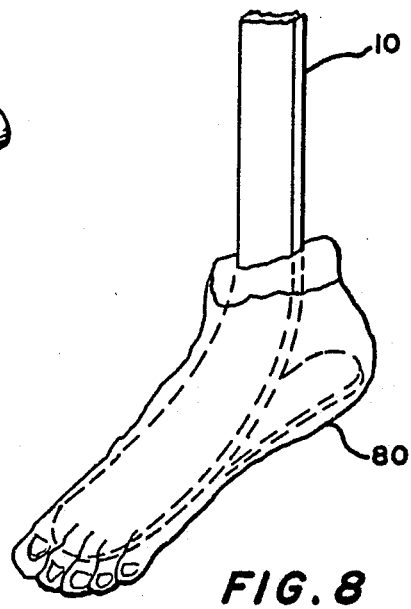

On devices subjected to rigorous impact and abrasion during use as in athletics, rock climbing, etc, the invention can be manufactured with a molded plastic shell 80, FIG. 8, formed to the appropriate foot contour directly on the device. This molding process surrounding the one piece laminate protects the construction from abrasive damage and is considerably more resistant to tearing or separation than cosmetic foam adhesive bonded builups typical of prior art.

Other or further finishing of the prosthesis of the present invention to cosmetically improve the aesthetics when worn in public is done in any presently known manner, such as by use of premolded or preshaped foam or rubber, or of flexible foam blocks affixed to the device by adhesive and shaped by sanding tools to match the natural limb. FIGS. 1 and 2 illustrate with phantom lines a typical finished configuration.

The prosthesis foot of the present invention has been fabricated in the embodiments of FIGS. 1 and 6. Both embodiments were fitted to a recreationally active amputee and subjected to rigorous use in athletic sports and daily use. The present invention was described by the wearer as functioning very well, having uniform stiffness transition throughout the walking and running gait. Other prior art of the energy storage/release type were described by comparison as being too stiff in the toe or ankle where attachment fasteners were installed. During the previous three years, the subject wearer had broken 6 prosthesis of the prior art energy storage type all at the heel attachment to the ankle.

Figure 9:
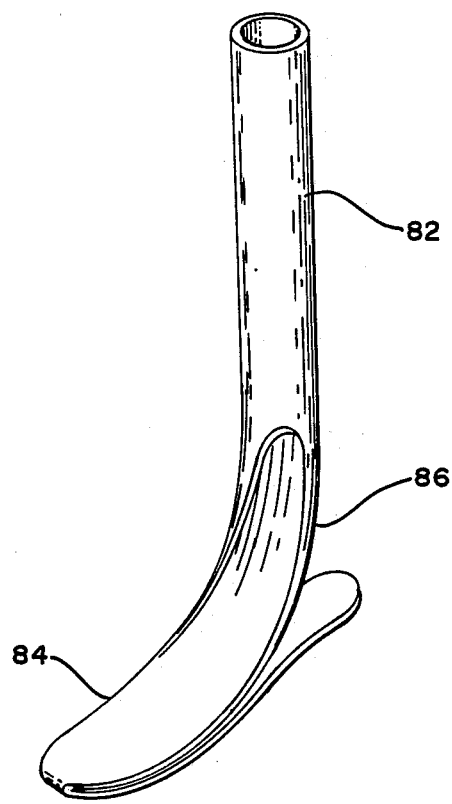

An alternate embodiment of the prosthesis of the invention is shown in FIG. 9. The leg section 82 of this embodiment is tubular in cross section. This configuration enables a very narrow width while exceeding the strength and stiffness properties possible with rectangular or square constructions of the same sectional area. The circular section also fits well into the receiving recess of housing 70 to maintaining interchangeability. In the embodiment of FIG. 9, the toe section 84 transitions to the alternate leg section 82 through the ankle area 86, as shown.

The invention also includes the method of producing a foot prosthesis by laying up the main member and heel member in uncured composite material and filling in the area between the toe section of the main member and the heel section, where the two are generally adjacent, with uncured rubber, such as green natural rubber, and then curing the composite and rubber material together to achieve a good bond between the composite material and the rubber. The rubber is preferably inserted and built up by layers of thin sheets of the rubber stacked on one another to fill in the desired area.

Whereas this invention is here illustrated and described with specific reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A foot prosthesis comprising an elongate composite main member having a leg section, a toe section, and a heel member, one end of said leg section being adapted to be connected to an amputation socket, the other end smoothly curving forwardly into the toe section which extends forwardly of the leg section to a toe end and then curving sharply rearwardly and extending rearwardly from the toe end substantially along and generally adjacent to the toe section to a point of divergence from where the heel member continues rearwardly to a heel tip while the toe section curves upwardly to the leg section; and resilient material adhered between the toe section and the heel member substantially through the area where the two are generally adjacent to restrain and control relative movement between the adjacent toe section and heel member.

2. A foot prosthesis according to claim 1, wherein the composite construction includes fibers embedded in matrix material.

3. A foot prosthesis according to claim 2, wherein at least some of the fibers are arranged to extend as continuous fibers from the end of the elongate main member adapted to be connected to the amputation socket to the toe end of the main member and then through the heel member to the heel tip.

4. A foot prosthesis according to claim 3, wherein the main member has a central composite core with the fibers in the core extending generally along the length of the member and an outer layer of composite material wherein the fibers extend generally at an angle to the length of the member.

5. A foot prosthesis according to claim 4, wherein the outer layer of composite material surrounds the core of composite material.

6. A foot prosthesis accoridng to claim 5, wherein the properties of the resilient material in the area where the toe section and heel member diverge is adjustable.

7. A foot prosthesis according to claim 6, wherein a recess is formed in the resilient material in the area where the toe section and heel member diverge, and wherein the recess is adapted to receive a plug therein, whereby receipt of plugs therein of differing properties will impart differing properties to the prosthesis.

8. A foot prosthesis according to claim 1, wherein the properties of the resilient material in the area where the toe section and heel member diverge is adjustable.

9. A foot prosthesis according to claim 8, wherein a recess is formed in the resilient material in the area where the toe section and heel member diverge, and wherein the recess is adapted to receive a plug therein, whereby receipt of plugs therein of differing properties will impart differing properties to the prosthesis.

10. A foot prosthesis according to claim 1, wherein the end of the elongate member adapted to be connected to the amputation socket is adapted to be removably connected to the amputation socket.

11. A foot prosthesis according to claim 10, wherein a prosthesis receiving recess is secured to the amputation socket and the end of the elongate member is adapted to slide into and out of the prosthesis receiving recess and, when in said recess, to be held firmly by said recess.

12. A foot prosthesis according to claim 1, wherein the resilient material is rubber.

13. A foot prosthesis according to claim 1, wherein the composite main member is formed by laying up an uncured composite main member, uncured rubber is placed between the toe section and heel member where the two are generally adjacent to form the resilient material, and the uncured composite material and uncured rubber are cured together to adhere the resilient material to the main member.

14. A foot prosthesis according to claim 13, wherein the uncured rubber is built up between the toe section and heel member using a plurality of sheets of uncured rubber.

15. A foot prosthesis according to claim 13, wherein a metal plug is inserted into the uncured rubber and remains in place during curing, after which the metal plug is removed to form a receiving recess in the cured rubber adapted to receive plugs which may be inserted thereinto by a wearer.

* * * * *